United States Patent
Ronnberg

(10) Patent No.: US 6,494,870 B1
(45) Date of Patent: Dec. 17, 2002

(54) OUTER SURFACE SHEET FOR ABSORBENT ARTICLES THAT INCLUDE BARRIER FLAPS

(75) Inventor: Peter Ronnberg, Molndal (SE)

(73) Assignee: SCA Hygiene Products AB, Gothenburg (SE)

(*) Notice: Subject to any disclaimer, the term of this patent is extended or adjusted under 35 U.S.C. 154(b) by 0 days.

(21) Appl. No.: 09/786,376
(22) PCT Filed: Aug. 25, 1999
(86) PCT No.: PCT/SE99/01456
§ 371 (c)(1), (2), (4) Date: May 8, 2001
(87) PCT Pub. No.: WO00/13634
PCT Pub. Date: Mar. 16, 2000

(30) Foreign Application Priority Data

Sep. 2, 1998 (SE) .............................. 9802961

(51) Int. Cl.[7] ............................................ A61F 13/15
(52) U.S. Cl. ............ 604/385.01; 604/358; 604/385.27; 604/385.28
(58) Field of Search .................... 604/358, 385.01, 604/385.27, 385.28

(56) References Cited

U.S. PATENT DOCUMENTS

| 5,087,255 A | * 2/1992 | Sims .................. 604/385.01 |
|---|---|---|
| 5,445,627 A | 8/1995 | Mizutani et al. |
| 5,569,234 A | 10/1996 | Buell et al. |
| 5,624,425 A | 4/1997 | Gray et al. |
| 5,814,035 A | 9/1998 | Gryskiewicz et al. |

FOREIGN PATENT DOCUMENTS

| EP | 0 625 346 | 11/1994 |
|---|---|---|
| WO | WO 96/07382 | 3/1996 |

\* cited by examiner

Primary Examiner—John J. Calvert
Assistant Examiner—Angela J. Grayson
(74) Attorney, Agent, or Firm—Young & Thompson

(57) ABSTRACT

An outer surface sheet (1) for absorbent articles, such as diapers, incontinence protectors or sanitary napkins, and comprises at least one upstanding barrier flap (5, 6) which extends across at least a part of the surface sheet. The surface sheet includes at least two parts (7, 8, 9) which are disposed to that bordering edge portions overlap each other. The barrier flap (5, 6) is comprised of a strip of elastic material that has two long edge portions and two end edge portions, wherein one of the long edge portions of said strip is inserted in a stretched state between the mutually overlapping edge portions of the two surface sheet parts (7, 8 and 7, 9 respectively) and firmly secured there-between.

10 Claims, 2 Drawing Sheets

OUTER SURFACE SHEET FOR ABSORBENT ARTICLES THAT INCLUDE BARRIER FLAPS

FIELD OF INVENTION

The present invention relates to an outer surface sheet for absorbent articles, such as diapers, incontinence protectors or sanitary napkins, comprising a central part and two side parts of inelastic materials, each of said parts having two longitudinal edge portions and adjacent longitudinal edge portions of the central part and the respective side part are mutually overlapping each other; and further comprising a barrier flap extending along at least a part of each of the longitudinal edge portions of the central part

BACKGROUND OF THE INVENTION

The outer surface sheets of absorbent articles of the aforementioned kind will often include so-called barrier flaps on that side of the article which lies proximal to the wearer's body in use. The prime purpose of the barrier flaps is to prevent liquid from running over the upper side of the surface sheet and out to the edges of the absorbent article. The flaps also form together with the surface sheet a basin-shaped cavity in which discharged liquid is stored temporarily before the absorbent body has been able to absorb the liquid discharged. This temporary storage space is particularly important with regard to incontinence protectors for adult persons, since the volume of liquid that is discharged onto such a product at one and the same time can be relatively large. In order to ensure that the liquid stored temporarily in this storage space will not leak from the article, it is necessary for the barrier flaps to lie sealingly against the body of the person wearing an absorbent article that includes barrier flaps on its outer surface sheet. Barrier flaps are often comprised of elongated pieces of inelastic material that are made elastic along one longitudinal edge part with the aid of pretensioned elastic threads. Such flaps are fastened to the outer surface sheet with the elastic threads in a stretched state. When these elastic threads are then allowed to relax, the flaps will take an upstanding position relative to the plane of the surface sheet. One problem with flaps of this nature is that the inelastic material in the flaps will pucker as the elastic threads contract. This puckering, or gathering, of the inelastic material means that the puckered longitudinal edges of the flaps will not seal effectively against the wearer's body when an article that includes an outer surface sheet on which such flaps are provided is worn.

It is known from Applicant's Swedish Patent Application No. 9700694-4, filed Feb. 27, 1997, to produce barrier flaps from elastic band material that has a generally smooth abutment surface in both a stretched and relaxed state. One problem encountered with the use of flaps comprised of elastic material is the difficulty experienced in fastening the flaps to the outer surface sheet. This problem has been solved in the aforesaid Swedish Patent Application by using a three-ply film that comprises two polypropylene outer layers and an intermediate layer of elastic film.

EP-A1-0 625 346 discloses a surface sheet according to the introductory part of the description.

An object of the present invention is to provide an outer surface sheet for absorbent articles that includes elastic barrier flaps which are fastened to the outer sheet in a manner such as to enable the use of flaps that consist solely of elastic material. Another object of the invention is to provide such a surface sheet of flexible construction that can be produced in a cost-effective manner without complicating the process of manufacturing the absorbent articles in which the outer surface sheet shall be included.

SUMMARY OF THE INVENTION

These objects are achieved with an outer surface sheet according to the introductory part of the description characterised in that the barrier flaps each is comprised of a strip of elastic material having two long edge portions and two end edge portions, wherein one of the long edge portions of each of said strips is inserted between the overlapping longitudinal edge portions of the coal part and respective side part and firmly secured therebetween. Because the elastic barrier flaps are fastened between two inelastic materials, it is easy to produce a secure attachment of the barrier flaps, regardless of whether the flaps are glued or welded in place. Furthermore, the division of the outer surface sheet into separate parts enables the outer sheet to be given a flexible construction by virtue of the fact that the different parts of said sheet may be comprised of different materials.

In one preferred embodiment of the invention, that longitudinal part of the strip which lies between the mutually overlapping longitudinal edge parts of the surface sheet parts is fastened to each of said overlapping parts.

According to a more preferred embodiment of the invention, the surface sheet parts are made of a heat-weldable material and the mutually overlapping longitudinal edge parts of the surface sheet parts are joined together by ultrasound welding or heat welding. The overlapping edge portions of the surface sheet parts are joined together through the longitudinal edge part of the stretched elastic strip sandwiched therebetween. The surface sheet will preferably comprise three separate longitudinal parts, two side parts and a central part, wherein at least the central part will comprise a liquid permeable material, and a barrier flap will extend along the two long edges of said central part. In one variant, the two side parts of the surface sheet are comprised of liquid impervious material and the mutually overlapping longitudinal edge portions of the side parts are placed on top of respective longitudinal edge portions of the central part. Each barrier flap is preferably comprised of a strip of elastic plastic film and tapers or narrows in a direction towards its end parts. Alternatively, the barrier flaps may taper from their end parts towards their centre part.

In one variant, at least one barrier flap extends in the transversal direction of the outer surface sheet.

BRIEF DESCRIPTION OF THE DRAWINGS

The present invention will now be described in more detail with reference to exemplifying embodiments thereof and also with reference to the accompanying drawings, in which.

DESCRIPTION OF EMBODIMENTS OF THE INVENTION

Figure 1:
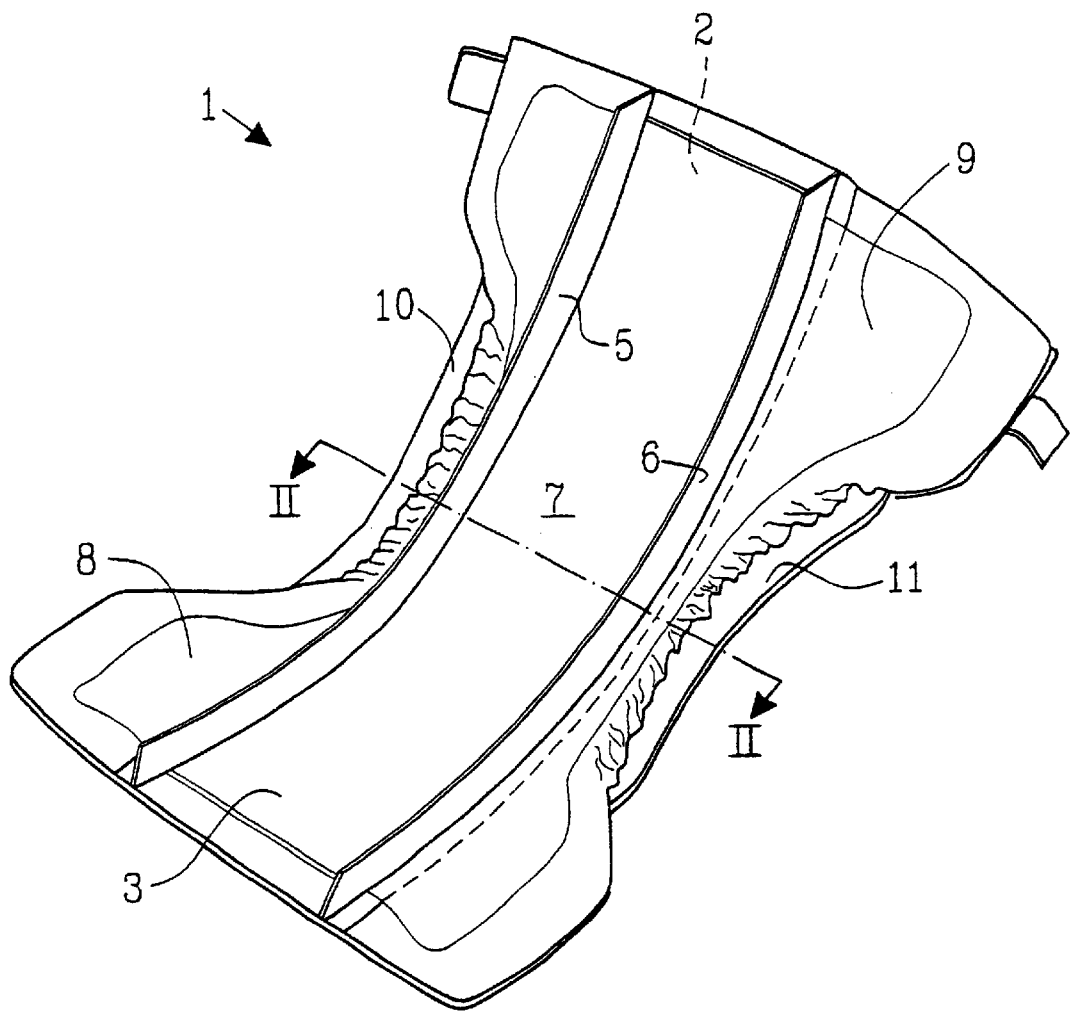
FIG. 1 is a schematic perspective view, shown obliquely from above, of an incontinence protector that includes an outer surface sheet according to the invention.
Figure 2:
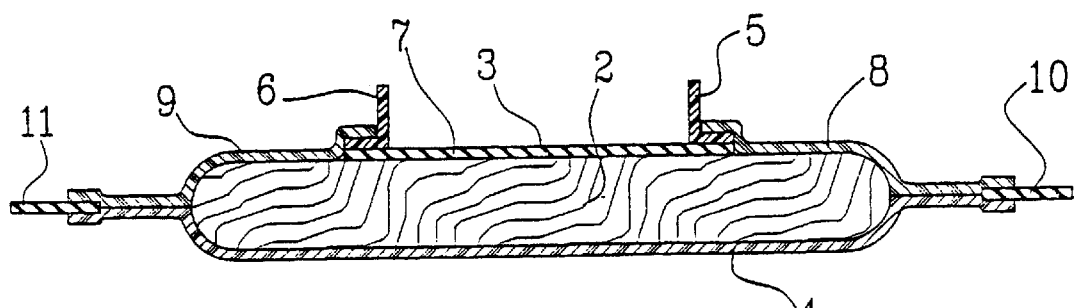
FIG. 2 is a cross-sectional view taken on the line II—II in FIG. 1.

FIGS. 1 and 2 illustrate an incontinence protector 1 for persons suffering from light incontinence. The incontinence protector 1 typically includes an absorbent body or core 2 which is sandwiched between a liquid-permeable outer surface sheet 3 and a liquid-impermeable outer backing sheet 4. The sheets 3 and 4 are mutually joined along sheet parts that lie outside the absorbent body 2. The incontinence protector 1 also includes two longitudinally extending barrier flaps 5, 6 which extend along the full length of the article in spaced relationship with the longitudinal edges of the absorbent body.

According to the invention, the liquid-permeable surface sheet 3 is comprised of a central part 7 and two side parts 8, 9. The longitudinal edge portions of the side parts 8, 9 that border on the central part 7 are disposed so as to overlap respective longitudinal edges of said central part 7. One of the longitudinal edge portions of the barrier flaps 5, 6 is disposed between the mutually overlapping longitudinal edge portions of the central part 7 and respective side parts 8, 9 and the mutually overlapping longitudinal edge portions of the central part 7, the side parts 8, 9 and the barrier flaps 5, 6 are glued or welded together.

The incontinence protector 1 also includes leg elastic in the form of two elastic strips 10, 11 that are fastened between the outer sheets 3, 4—as will be best seen from FIG. 2.

In the illustrated embodiment, the absorbent body 1 is comprised of cellulose fluff either with or without an admixture of so-called superabsorbent particles. However, the absorbent body may comprise any material, or materials, used in absorbent bodies for absorbent articles of the kind mentioned in the introduction. The absorbent body may alternatively be comprised of more than one layer of absorbent material, and may even include layers of wadding or like material so as to quickly remove discharged liquid from the liquid receiving outer surface sheet.

The liquid impermeable sheet will preferably be made of plastic film, for example polyethylene film, although all other materials used as liquid impermeable sheet material for absorbent articles may, of course, be used.

The central part 7 of the liquid impermeable outer surface sheet 3 will preferably consist of perforated plastic film or nonwoven material, although it will be understood that any material used for producing liquid permeable outer sheets for absorbent articles of the aforesaid kind may, of course, be used. The side parts 8, 9 may consist of the same material as the central part 7, although said side parts 8, 9 will preferably be comprised of a liquid impermeable material. In this latter case, these side parts will then function as edge seals and enhance safety against side edge leakage.

The barrier flaps are made of an elastic material, for example elastic film. The elastic material used in the barrier flaps may be based on styrene block copolymers, such as styrene-butadiene-styrene (SBS), styrene-isoprene-styrene (SIS), styrene-ethene-butene-styrene (SEBS) or styrene-ethene-propene-styrene (SEPS). The elastic material may also comprise several layers, provided that the layer material will not pucker as the material contracts or relaxes.

It is normally difficult to weld elastic film to inelastic material, owing to the different melting points of the different polymers included in the materials. Problems are also experienced when gluing elastic film to inelastic material, due to the shear forces occurring in the join. These difficulties are overcome in accordance with the invention, by sandwiching the attachment part of the elastic material between two layers of inelastic material. This enables the two layers of inelastic material to be spot-welded to one another, through the elastic material. Distribution of the stresses in the glue joints is also enhanced in that case when the elastic material is glued to both inelastic material layers between which the elastic material is inserted.

Because the barrier layers are fastened to two layers of inelastic material, that part of the outer surface sheet located within the join regions of the barrier flaps will be stiffer than the remainder of the sheet. This reduces the risk of the outer surface sheet puckering when the elastic barrier flaps contract subsequent to manufacture of the described incontinence protector.

Fastening of the barrier flaps between two layers of inelastic material as described above provides a wide choice of material from which the barrier flaps can be made, since it is not necessary to take the weldability of the flaps to other materials in the outer surface sheet into account when choosing said material. The inventive fastening principle may, of course, also be applied with barrier flaps that are not fully elastic, for example conventional barrier flaps having free edge parts that have been made elastic with the aid of prestretched elastic threads, or barrier flaps made of elastic shrink film.

Figure 3:
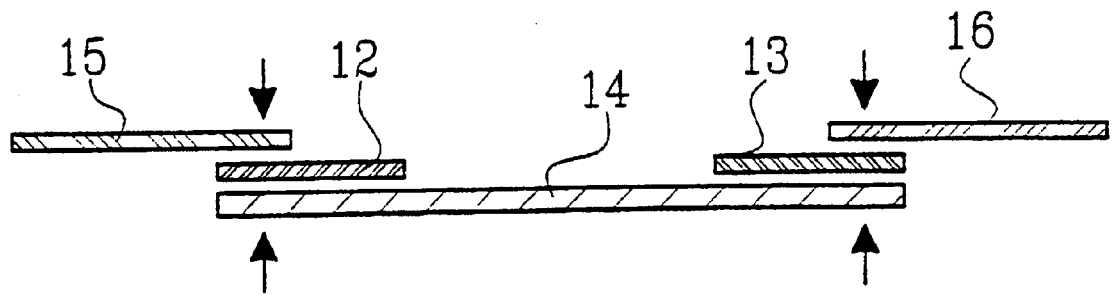
FIG. 3 is a cross-sectional view illustrating a first method of producing an inventive outer surface sheet.

FIG. 3 illustrates schematically a method of manufacturing the outer surface sheet 3 shown in FIGS. 1 and 2. The sheet 3 is manufactured simply by laying prestretched, elongated strips or bands 12, 13 on a first web 14 of heat-weldable, liquid-permeable material, such that the outer edges of the strips or bands 12, 13 and the material web 14 will lie edge to edge. Elongated second webs 15, 16 of heat-weldable material are then applied, so that the inner long-edge portions of the second webs 15, 16 overlap the long edge portions of the strips 12, 13 and the first web 14. The mutually overlapping portions of the first web 14, the strips 12, 13 and the second webs 15, 16 are then passed through the nip defined between an ultrasound horn of an ultrasound welding unit and an anvil means, as indicated schematically by arrows in FIG. 3, therewith joining these components together.

The described method of manufacture is well suited to the continuous manufacture of the outer surface sheets of absorbent articles provided with barrier flaps. For instance, outer surface sheets can be prefabricated and then reeled up onto storage reels which can be placed in position in a production line for the manufacture of absorbent articles, such as incontinence protectors, for instance. The manufacture of outer surface sheets provided with barrier flaps may alternatively take place in the production line and said surface sheet introduced into the production line immediately the mutually overlapping portions of the first material web, the elastic strips and the second material webs have been joined together in the manner described. A thus produced outer surface sheet is, for instance, placed on a web of liquid impermeable material subsequent to having placed a line of absorbent bodies on said material.

The last manufacturing stage in such an incontinence protector production line comprises cutting separate incontinence protectors from the continuous composite web of outer sheets and intermediate absorbent bodies. Subsequent to having cut individual incontinence protectors from the production line, the barrier flaps, which have been kept stretched during the entire manufacturing process, can be allowed to relax and therewith take a position in which they are upstanding relative to the liquid-permeable outer surface sheet, as shown in FIGS. 1 and 2.

Figure 4:
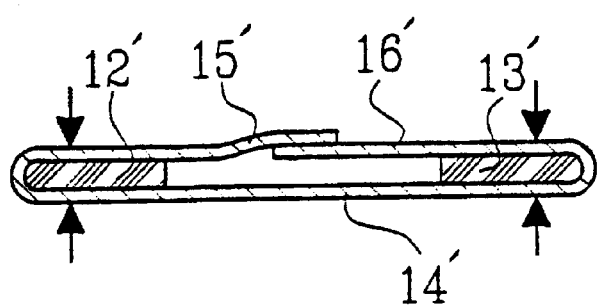
FIGS. 4 and 5 are respective cross-sectional views illustrating a second method of producing an inventive outer surface sheet.
Figure 5:
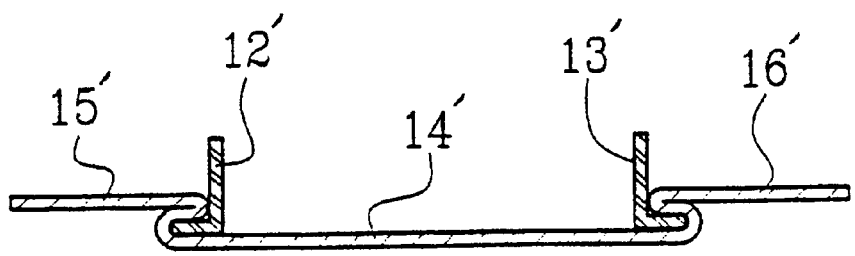

FIGS. 4 and 5 illustrate another method of manufacturing an outer surface sheet in accordance with the invention. As in the earlier described method, two prestretched strips 12', 13' are placed on top of a web 14' of liquid-permeable and heat-weldable material. In this embodiment, however, the strips 12', 13' are spaced slightly from the respective side edges of the web 14'. Those portions 15', 16' of the web 14' that lie outside the outer extremities of the strips 12', 13' are then folded in over said strips 12', 13' and the central part of the web 14', in the manner shown in FIG. 4, whereafter the outer edge portions of the strips 12', 13' are welded to the outer edge portions of the central part of the web 14' and to the outer edge portions of the inwardly folded parts 15', 16' of the web 14', as indicated by arrows in FIG. 4. The web portions 15', 16' are then folded back, as shown in FIG. 5. FIG. 5 shows the manufactured outer surface sheet with barrier flaps 12', 13' in its contracted state.

It will be understood that the aforedescribed embodiments of an outer surface sheet may be modified within the scope of the invention. For instance, the barrier flaps need not extend along the full length of the surface sheet. Neither need the free long edge portions of the barrier flaps extend rectilinearly, but may, in principle, have any shape whatsoever, for instance the height of the barrier flaps may be shorter at the end parts of the surface sheet than in its longitudinal centre part. The strips or bands forming the barrier flaps may be configured so that they will exhibit curved fastener parts when stretched, while giving the long-edge portions of the central part of the surface sheet and its side parts a corresponding curvature. Although the described embodiments include solely barrier flaps that extend in the longitudinal direction of the outer surface sheet it will be understood, of course, that barrier flaps that extend transversely of the outer sheet may also be included. The invention is therefore only restricted by the contents of the accompanying claims.

What is claimed is:

1. An outer surface sheet for absorbent articles (1), comprising a central part (7) and two side parts (8,9) of inelastic materials, each of said parts having two longitudinal edge portions and adjacent longitudinal edge portions of the central part (7) and the respective side part (8,9) are mutually overlapping each other, and further comprising a barrier flap (5,6) extending along at least apart of each of the longitudinal edge portions of the central part, characterised in that the barrier flaps (5,6) each is comprised of a strip of elastic material having two long edge portions and two end edge portions, wherein one of the long edge portions of each of said strips is inserted in a stretched state between the overlapping longitudinal edge portions of the central part (7) and respective side part (8,9) and firmly secured therebetween.

2. A surface sheet according to claim 1, characterised in the long edge portion of each strip (5,6) located between the respective overlapping longitudinal edge portions of the central part (7) and the respective side part (8,9) is fastened to both of said overlapping longitudinal edge portions.

3. A surface sheet according to claim 1, characterised in that the central part (7) and the side parts (8,9) of the surface sheet are comprised of heat-weldable material; and in that the mutually overlapping longitudinal edge portions of the central part (7) and the respective side part (8,9) are joined together by ultrasound welding or heat welding.

4. A surface sheet according to claim 3, characterised in that the overlapping longitudinal edge portions of the central part (7) and the side parts (8,9) are fastened together through the long edge portion of the prestretched elastic strip (5,6) located therebetween.

5. A surface sheet according to claim 1, characterised in that at least the central part (7) of the surface sheet (7, 8, 9) is comprised of a liquid permeable material.

6. A surface sheet according to claim 5, characterised in that the two side parts (8,9) of the surface sheet are comprised of a liquid impermeable material.

7. A surface sheet according to claim 1, characterised in that each barrier flap (5, 6) is comprised of a strip of elastic plastic film.

8. A surface sheet according to claim 1, characterised in that the barrier flaps taper in a direction towards their respective end edge portions.

9. A surface sheet according to claim 1, characterised in that the barrier flaps taper from their respective end edge portions in towards their respective centre portions.

10. A surface sheet according to claim 1, characterised in that at least one barrier flap extends transversely across said surface sheet.

* * * * *